(12) United States Patent
Jost et al.

(10) Patent No.: US 9,850,513 B2
(45) Date of Patent: Dec. 26, 2017

(54) METHOD FOR INCREASING THE SECRETION OF RECOMBINANT PROTEINS

(71) Applicant: GREENOVATION BIOTECH GMBH, Freiburg (DE)

(72) Inventors: Wolfgang Jost, Freiburg (DE); Mathias Knappenberger, Mietingen/Baltringen (DE); Doreen Claussnitzer, Munich (DE); Andreas Schaaf, Freiburg (DE)

(73) Assignee: GREENOVATION BIOTECH GMBH, Freiburg (DE)

( * ) Notice: Subject to any disclaimer, the term of this patent is extended or adjusted under 35 U.S.C. 154(b) by 0 days.

(21) Appl. No.: 14/394,991

(22) PCT Filed: Apr. 17, 2013

(86) PCT No.: PCT/EP2013/057956
§ 371 (c)(1),
(2) Date: Oct. 16, 2014

(87) PCT Pub. No.: WO2013/156504
PCT Pub. Date: Oct. 24, 2013

(65) Prior Publication Data
US 2015/0079632 A1 Mar. 19, 2015

(30) Foreign Application Priority Data
Apr. 17, 2012 (EP) .................... 12164458

(51) Int. Cl.
| | |
|---|---|
| C12N 5/02 | (2006.01) |
| C12N 5/14 | (2006.01) |
| C12P 21/00 | (2006.01) |
| C12P 21/02 | (2006.01) |
| C12N 5/00 | (2006.01) |
| C12N 1/12 | (2006.01) |
| C12N 1/14 | (2006.01) |

(52) U.S. Cl.
CPC ............... *C12P 21/00* (2013.01); *C12N 1/12* (2013.01); *C12N 1/14* (2013.01); *C12N 5/0025* (2013.01); *C12P 21/02* (2013.01); *C12N 2500/60* (2013.01)

(58) Field of Classification Search
None
See application file for complete search history.

(56) References Cited

U.S. PATENT DOCUMENTS

2010/0035327 A1* 2/2010 Steele et al. ............... 435/235.1

FOREIGN PATENT DOCUMENTS

| CN | 1280186 A | 1/2001 |
| WO | WO 03/083066 A2 | 10/2003 |

OTHER PUBLICATIONS

Choksakulnimitr et al. (Journal of Controlled Release 34 (1995) 233-241).*
James et al. (Protein Expression and Purification 19, 131-138 (2000)).*
Magnuson et al. (Protein Expression and Purification 7, 220-228 (1996)).*
Murashige et al. (Physiologia Plantarum, vol. 15. 1962, 473-497).*
Madhusudhan et al. (Indian Journal of Experimental Biology vol. 37, Jan. 1999, pp. 66-69).*
Hellwig et al. (Nature Biotechnology vol. 22 No. 11 Nov. 2004, p. 1415-1422).*
Lee et al. (Biotechnology Letters, vol. 19, No. 1, Jan. 1997, pp. 93-96).*
Groll et al. (Annals of Botany 89:645-648, 2002).*
LaCount et al. (Biotechnology Letters, vol. 19, No. 1, Jan. 1997, pp. 93-96).*
Carpita (Plant Physiol. (1985) 79, 485-488).*
Cooper (The Cell: A Molecular Approach. 2nd edition. Sunderland (MA): Sinauer Associates; 2000. Cell Walls and the Extracellular Matrix. Available from: https://www.ncbi.nlm.nih.gov/books/NBK9874/, retrieved Jan. 6, 2016).*
Baur et al., A fast and flexible PEG-mediated transient expression system in plants for high level expression of secreted recombinant proteins, Journal of Biotechnology 119, pp. 332-342, (2005).
Baur et al., "Enhanced recovery of a secreted recombinant human growth factor using stabilizing additives and by co-expression of human serum albumin in the moss Physcomitrella patens", Plant Biotechnology Journal, Bd. 3, Nr. 3, pp. 331-340, (2005).
David et al., "Optimization of antibody fragment production in Bacillus megaterium: The role of metal ions on protein secretion", Journal of Biotechnology 150, pp. 115-124, (2010).
Decker et al., "Current achievements in the production of complex biopharmacueticals with moss bioreactors", Bioprocess Biosyst Eng vol. 31, pp. 3-9, (2008).
Drake et al., "Rhizosecretion of a monoclonal antibody protein complex from transgenic tobacco roots", Plant Molecular Bilology 52: pp. 233-241, (2003).
Gaume et al., "Rhizosecretion of recomibinant proteins from plant hairy roots", Plant Cell Rep, 21, pp. 1188-1193, (2003).
Komarnytsky et al., "Production of Recombinant Proteins in Tobacco Guttation Fluid", Plant Physiology, vol. 124, pp. 927-933, Nov. 2000.
Kwon et al., "Expression and Secretion of the Heterodimeric Protein Interleukin-12 in Plant Cell Suspension Culture", Wiley Periodicals, Inc., pp. 870-875, (2003).
LaCount et al., "The effect of polyvinylpyrrolidone (PVP) on the heavy chain monoclonal antibody production from plant suspension cultures", Biotechnology Letters, vol. 19, No. 1, pp. 93-96, Jan. 1997.

(Continued)

Primary Examiner — Elizabeth McElwain
Assistant Examiner — Charles Logsdon
(74) Attorney, Agent, or Firm — Birch, Stewart, Kolasch & Birch, LLP

(57) ABSTRACT

The invention relates to a method for producing a recombinant protein in cells with a cell wall, comprising the step of increasing the secretion of the recombinant protein through the cell wall by expression of the protein in the cells in a culture medium containing a combination of a surface-active polymer and monovalent metal ions and with an osmolarity at least 0.32 osmol/L, said invention further relating to culture media and nutrient mixtures for the method.

21 Claims, 2 Drawing Sheets

(56) References Cited

OTHER PUBLICATIONS

Lee et al., "Increased production of human granulocyte-macrophage colony stimulating factor (hGM-CSF) by the addition of stabilizing polymer in plant suspension cultures", Journal of Biotechnology 96, pp. 205-211, (2002).
Lee et al., "Stimulation of murine granulocyte macrophage-colony stimulating factor production by Pluronic F-68 and polyethylene glycol in transgenic Nicotiana tabacum cell culture", Biotechnology Letters 24, pp. 1779-1783, (2002).
Magnuson et al., "Enhanced Recovery of a Secreted Mammlian Protein from Suspension Culture of Genetically Modified Tobacco Cells", Protein Expression and Purification 7, pp. 220-228, (1996).
Schuster et al., In vivo glyco-engineered anitbody with improved lytic potential produced by an innovative non-mammalian expression system, Biotechnol. J. 2, pp. 1-9, (2007).
Tsoi et al., "Effect of medium properties and additives on antibody stability and accumulation in suspended plant cell cultures", Biotechnol. Appl. Biochem. 35, pp. 171-180, (2002).
Twyman et al., "Molecular farming in plants: host systems and expression technology", Trends in Biotechnology, vol. 21, No. 12, pp. 570-578, Dec. 2003.
English language translation of the International Preliminary Report on Patentability Written Opinion, dated Oct. 21, 2014.
Chinese Office Action issued in Chinese Patent Application No. 201380020538.2 dated Sep. 6, 2015.
European Office Action dated Nov. 25, 2015, for European Application No. 13717769.7.

\* cited by examiner

METHOD FOR INCREASING THE SECRETION OF RECOMBINANT PROTEINS

The present invention relates to the optimization of recombinant plant or fungal expression systems with the aid of suitable expression methods.

The production of recombinant proteins in a concentration range of ng/l to µg/l in plants has already been described in a number of publications. The publication WO 01/25456 A2 relates to a method for the production of proteins that are present in moss without lysing the moss tissues or moss cells and in addition mentions that the productivity may be increased by the use of PVP in a culture medium. By way of example, this is shown for the recombinant production of $VEGF_{121}$, a small glycosylated homodimer with a size of 28 kDa (Baur et al., Journal of Biotechnology 119 (2005): 332-342). Baur et al. describe the transient transformation of moss using PEG. The medium employed for the production of VEGF was free of PVP or PEG.

Drake et al., Plant Mol. Biol. 52 (2003): 233-241, describe the recombinant expression of antibodies in a culture of tobacco plant tissue, i.e. of root tissue. The antibodies were secreted by a process of rhizosecretion in the microgram (µg) range. Effective plant expression systems based on rhizosecretion are mostly hairy root cultures that can be stimulated by infecting any type of plant with *Agrobacterium rhizogenes* (Gaume et al., Plant Cell Rep. 21 (2003): 1188-1193).

Komarnysky et al., Plant Physiology 124 (2000): 927-933, describe the secretion of recombinant proteins by the process of guttation, in which proteins are secreted in the guttation fluid of leaves. The daily production rates were in a range of 1 µg/g of leaf mass.

A tobacco suspension culture for the recombinant expression of heterologous proteins is described in Kwon et al., Biotechnology and Bioengineering 81(7) (2003): 870-875. Callus cells of transformed plants were used as a cell line for the production of human IL-12. As potential additives for the cell culture medium, three polymers were tested for their ability to stabilize IL-12. PVP and PEG had no effect, whereas gelatine resulted in a stabilization of IL-12 until day 5 of the culture, when proteases present in the medium led to a decrease of concentration. Similar results are described in Lee et al., Journal of Biotechnology 96 (2002): 205-211.

LaCount et al., Biotechnology Letters 19(1) (1997): 93-96, describe the stabilization of recombinantly produced antibodies and of GM-CSF, respectively, by a treatment with PVP for protection from protease degradation.

Lee and Kim, Biotechnology Letters 24 (2002): 1779-1783, describe the use of Pluronic F-68 and polyethylene glycol for protecting cells present in a tobacco suspension culture from mechanical damage in a stir-tank bioreactor.

Magnuson et al., Protein Expression and Purification 7, (1996): 220-228, describe the expression of a 50 kDa heavy chain of a monoclonal antibody in a suspension culture of tobacco cells. The addition of PVP to the culture medium resulted in a 35-fold increase in yield, which was ascribed to a stabilization of the protein as well as to the prevention of aggregation and accumulation on vascular walls. 66% of the protein were found in the cytoplasm, 30% in the membrane fraction and only 4% in the medium. Despite secretory signal sequences which only signal a passage through the cell membrane, large protein molecules having a molecular mass of more than 50 kDa were considered too large for passages through the cell wall.

Schuster et al., Biotechnol. J. 2 (2002): 1-9, describe the production of an antibody in moss protoplasts. By culturing in a mixture of 3M and W5 medium in combination with a previous efficiency-enhanced transformation according to Baur et al. (supra) the yield was increased from 0.1-0.5 µg/ml to 8.2 µg/ml.

Tsoi and Doran, Biotechnol. Appl. Biochem. 35 (2002): 171-180, describe various expression media and their respective influence on the expression of antibodies by suspension cultures of tobacco cells. The yield of the secreted antibodies was between 20 and 200 µg/50 ml of culture medium.

Document US 2010/035327 A1 relates to a universal additive for culture media that is produced from rice polysaccharides and polypeptides and supposedly enhances both growth and secretion of cell products. However, the problem of secretion through a cell wall is not addressed therein.

David et al., Journal of Biotechnology 150 (1) (2010): 115-124, relates to the recombinant production of antibody fragments in *Bacillus megaterium*, i.e. a cell that has no cell wall.

Baur et al., Plant Biotechnology Journal 3 (3) (2005): 331-340, describe *P. patens* as an expression system as well as an increased secretion of recombinant human growth factor (VEGF) by the use of additives (PVP) and by the expression of human serum albumin.

Decker et al., Bioprocess and Biosystems Engineering, Jan. 31 (1) (2008): 3-9, generally discuss culture conditions in moss bioreactors and plant-specific glycoengineering.

Twyman et al., Trends in Biotechnology 21 (12) (2003): 570-578, explain the use of plants as recombinant expression systems. Transfection systems, signal sequences and mRNA stability are discussed with respect to yield.

Despite the availability of known methods for increasing the productivity of plants and plant cells in the recombinant production of heterologous proteins, plant systems are still less productive than animal cells, such as for example established CHO expression systems. Thus, there is a constant need to further increase the productivity of plant expression systems. Moreover, the production of secreted proteins is desirable, so that the producing cells need not be destroyed and can be used for further production.

It is therefore an object of the present invention to provide improved expression methods as well as means therefor.

The present invention relates to a method for producing a recombinant protein in cells having a cell wall, comprising the step of secreting the recombinant protein through the cell wall by means of expressing the protein present in the cells in a culture medium containing a combination of a surface-active polymer and monovalent metal ions and having an osmolarity of at least 0.22 osmol/L. Further aspects of the present invention are such culture media as well as material compositions. In particular, said step of secretion is an increase in secretion. Said increase is usually defined in comparison with untreated cells. Furthermore, the present invention is as defined in the appended claims. In the following, particular embodiments and preferably parameters are described, which may be provided in combination with one another.

A successful and inexpensive production of biopharmaceuticals requires a successful secretion of proteins as well as an increased amount of product [mg/l to g/l]. Moreover, cell walls act as a size exclusion filter due to their (macro-) molecular structure. In the production of recombinant proteins in plant or fungal cells, this fact prevents a secretion of products having a size of more than 90 kDa into the culture medium, which would be advantageous for further processing. While in fact the proteins produced in this manner, provided they are equipped with a secretory signal peptide, are transported across the cell membrane, they tend to accumulate in the apoplastic space, i.e. in the compartment located between the cell membrane and the outer border of the plant cell wall, however. The secretion of smaller proteins having at least 50 kDa is also decreased. Firstly, the present invention increases the production of proteins and, in addition, surprisingly enhances the secretion of said proteins. The proteins produced according to the present invention may be of any size, although the particular advantages are observed with larger proteins. Thus, the proteins produced according to the present invention preferably have a size of more than 40 kDa, more than 50 kDa, more than 55 kDa, more than 60 kDa, more than 65 kDa, more than 70 kDa, more than 75 kDa, more than 80 kDa, more than 85 kDa or more than 90 kDa. Said proteins may also be dimers or heteromers of such proteins.

The monovalent metal ions are preferably selected from alkali metal ions, such as Li, Na, K, Rb or Cs. Particularly preferably, said monovalent metal ions comprise or are Na ions.

Preferably the metal ion, e.g. the Na ion, is present in the medium in a concentration of at least 20 mM, particularly preferably in a concentration of at least 30 mM, at least 40 mM, at least 50 mM, at least 60 mM, at least 70 mM, at least 80 mM, at least 90 mM, or at least 100 mM. Preferably, the metal ion present in one of these concentrations is sodium.

The addition of the metal ion leads to an increase in osmolarity, thereby enhancing the secretion through the cell wall while at the same time causing considerable stress on the cell, which in turn results in a deceleration or complete arrest of cell growth. The production of protein is also decelerated. The osmolarity preferably is at least 0.33 osmol/L, at least 0.34 osmol/L, at least 0.35 osmol/L, at least 0.36 osmol/L, at least 0.37 osmol/L, at least 0.38 osmol/L or at least 0.4 osmol/L. In particular, the osmolarity is within a range of 0.32 osmol/L to 0.6 osmol/L or also of 0.35 osmol/L to 0.55 osmol/L.

A surface-active polymer is a substance that decreases the surface tension of a liquid or the interfacial tension between two phases and thus enables or facilitates the formation of a dispersion or is capable of acting as a solubilizer. It was surprisingly found that by using such a polymer in combination with a metal ion at a high osmolarity a significant increase in production could be achieved in the expression of secreted proteins in cells having a cell wall. In particular, the polymer is a non-ionic, water-soluble, surface-active polymer. Preferably, said polymer does not have a denaturing effect on proteins. Examples are polymers or copolymers selected from polyethers such as polyalkyl glycols, polysorbates or polyvinyl pyrrolidone, polyvinyl alcohol, water-soluble cellulose derivatives such as hydroxypropyl cellulose, hydroxypropylmethyl cellulose, carboxymethyl cellulose or hydroxyethyl cellulose, vinylpyrrolidone-vinyl acetate copolymer (copovidones), polyvinyl acetate, partially hydrolyzed polyvinyl alcohol, polyvinyl alcohol-polyethylene glycol copolymers and mixtures thereof.

Preferably, the proportion of carbonyl oxygen ($O=R_1$) and/or ether oxygen ($R_1-O-R_2$) present in the polymer is at least 1% by weight of the molar weight of the polymer. Without being limited to a specific theory, it appears that the presence of such oxygen groups in the polymer leads to a stabilization of the cell, so that the salt-containing medium having a high osmolarity is better tolerated and the productivity can thus be increased. Preferably, the proportion of carbonyl oxygen and ether oxygen present in the polymer is at least 1.5% by weight, at least 2.5% by weight, or at least 5% by weight, particularly preferably at least 10% by weight, at least 15% by weight, at least 20% by weight or at least 25% by weight. The proportion of carbonyl oxygen and ether oxygen present in the polymer preferably is between 1% by weight and 50% by weight, preferably between 10% by weight and 42% by weight, in particular between 5% by weight and 38% by weight, e. g. 36% by weight (only ether oxygen) in polyethylene glycol or 14.5% by weight (only carbonyl oxygen) in PVP.

The polyether preferably is a polymer or copolymer of a polyalkyl glycol, e. g. of polyethylene glycol (PEG) or of polypropylene glycol or polyethylene-polypropylene oxide copolymers. The polymerized alkyl may also be a mixture of individual alkylenes, e. g. as in a poloxamer. The alkyl is preferably selected from $C_1$-$C_8$ alkylene, in particular selected from $C_2$, $C_3$-, $C_4$-, $C_5$-, $C_6$-, $C_7$-alkylene or mixtures thereof. A polyalkyl glycol may be structured according to the formula $[-R-O-]_n$, wherein R represents the alkyl group. Terminal OH groups, ester or ether groups may independently be provided. The ester or ether groups may be independently selected from $C_1$-$C_8$ groups, as mentioned above, or from longer organic chains, such as e.g. $C_9$-$C_{18}$. The ester or ether groups may be linked via a linking group, preferably a $C_1$-$C_{12}$ linking group, such as e.g. an aryl group (e.g. in octoxynol (Triton X-100) or nonoxynol). The polyether or polyalkyl glycol preferably contains at least one OH group, preferably at least 2 OH groups, which can be terminal OH groups.

The molecular weight of the surface-active polymer, e.g. PEG and the like, preferably is at least 500 Da, particularly preferably at least 1,000 Da, at least 1,500 Da, at least 2,000 Da, at least 3,000 Da, at least 4,000 Da, at least 6,000 Da, at least 8,000 Da, at least 10,000 Da, at least 20,000 Da or at least 30,000 Da. Particularly preferably, the molecular weight is between 500 Da and 2,000,000 Da, preferably between 1,000 Da and 200,000 Da or between 1,200 Da and 80,000 Da.

The surface-active polymer is preferably present in a concentration of at least 0.05% by weight, particularly preferably of at least 0.08%, at least 0.1% or at least 1.5%, in the medium (all %-values refer to % by weight).

In particular embodiments, the cells are cultured in a suspension culture or a hydroponic culture, in particular in a hairy root culture. In order to increase their secretory activity, the secreting cells are treated with the medium according to the present invention.

With the cells according to the present invention, the secretion into the medium mostly occurs from the apoplastic space of the cell. For the secretion, optionally into the apoplastic space, the protein is usually expressed with a signal sequence for the apoplastic space or for the secretion. Suitable signal sequences are well known in the art, e.g. in the literature mentioned in the above, and can be used according to the present invention.

The method according to the present invention is particularly suitable for increasing the secretion of cells having a cell wall. Such cells can be selected from a plant cell, a fungal cell or an algae cell. The term "cell", as used herein, can relate to isolated cells, single cells or a cell in a multicellular organism. A plant cell may be a single plant cell or a cell in a plant or in a plant tissue. Analogously, a fungal cell can be a single fungal cell or a cell in a fungus or in a fungal tissue. The algae cell is preferably a green algae cell. Tissues can, e.g., be selected from phloem, xylem, mesophyll, stem, leaves, thallus, protonema, chloronema, caulonema, rhizoids or gametophores. The cells can comprise or consist of protoplasts or parenchymal cells, in particular callus cells.

The cell to be used in the method according to the present invention preferably is a plant cell, preferably obtained from a moss, in particular selected from the group consisting of mosses and liverworts, wherein the use of species from the genera *Physcomitrella, Funaria, Sphagnum* and *Ceratodon*, as well as *Marchantia* and *Sphaerocarpus*, respectively, is particularly preferred. Most preferably, the method according to the present invention is carried out with the use of cells, plants or plant tissue, such as protonema of the moss *Physcomitrella patens*. Further preferable plants are tobacco, beans or lentils. Preferably, the plant is an aquatic plant, e.g. of the genera *Lemna, Spirodela, Landoltia, Wolffia* or *Wolffiella*.

According to a further preferred embodiment of the present invention, the cell is cultivated in a culture medium that is essentially free of sugars, vitamins and phytohormones or functional fragments thereof. Examples of suitable phytohormones are growth hormones, such as e.g. auxins.

Preferably, the method according to the present invention is carried out under photoautotrophic growth conditions. The method according to the present invention facilitates the cultivation of complete and differentiated plants, plant cells or algae under standardizable photoautotrophic conditions, i.e. without the need for sugars, vitamins, phytohormones and the like.

Basically, it is of course also possible to use sugar, vitamins or phytohormones, in particular in media for fungal cells that are not capable of photoautotrophic growth. In case of fungal cells, a catabolic carbon source should be provided. Due to the autotrophic properties of the cells, the medium may be free of proteins. Preferably, the medium is a sterilized medium, so that the danger of infection will be reduced. The medium can also be supplemented with an antibiotic agent in order to protect the respective cell from pathogens afflicting such a cell.

The pH value of the culture medium preferably is between 3.5 and 8.5, particularly preferably between 4 and 8 or between 4.5 and 7 or between 5 and 6.5, in particular between 5.5 and 6, whereby the pH value is optimized for optimal growth or expression conditions.

In order to ensure optimal growth or an increased protein production, the medium should contain micronutrients for the respective cells, in particular mineral substances. The medium preferably comprises nitrate ions, preferably in a concentration of at least 0.2 mM, phosphate ions, preferably in a concentration of at least 0.05 mM, sulfate ions, preferably in a concentration of at least 0.02 mM, calcium ions, preferably in a concentration of at least 0.1 mM, potassium ions, preferably in a concentration of at least 0.1 mM, or combinations thereof. The medium can also contain sodium ions, preferably in a concentration of at least 20 mM.

In specific embodiments of the present invention, the method additionally comprises another step that is carried out prior to the above-mentioned step of (increasing the) secretion of the recombinant protein in the above-mentioned medium. In said preceding step, the cells are grown in a culture medium having an osmolarity of less than 0.1 osmol/L, in particular without the above-mentioned (increase in) secretion, whereby protein accumulates in the interior or in the apoplastic space of the cells. In particular, said preceding step enhances the protein expression, even if the secretion of these proteins is not increased under said conditions. By means of the following step of (increasing the) secretion, as described in the above, it is finally possible to secrete and harvest the proteins produced in increased amounts without destroying the cell. This two-step method facilitates a considerable increase in production.

The culture medium in said preceding step may basically have the same composition as the culture medium in the secretion step—albeit with a lower osmolarity due to the lower concentration of metal ions. The culture medium in the preceding step contains—analogously to or independently of the composition of the medium in the secretion step—nitrate ions, preferably in a concentration of at least 0.2 mM, phosphate ions, preferably in a concentration of at least 0.05 mM, sulfate ions, preferably in a concentration of at least 0.02 mM, calcium ions, preferably in a concentration of at least 0.1 mM, potassium ions, preferably in a concentration of at least 0.1 mM, or combinations thereof, thereby facilitating optimal cell growth. The maximal concentration of the sodium ions is 20 mM, particularly preferably 15 mM or 10 mM.

The culture medium in said preceding step is preferably free of surface-active polymer or contains the latter in a maximum concentration of 0.08% by weight or 0.01% by weight or 0.005% by weight.

In said preceding step, the culture medium can also essentially be free of sugars, vitamins and phytohormones or functional fragments thereof, although it may contain these substances in alternative embodiments. The culture medium can either be sterile or contain an antibiotic agent. The pH value of the culture medium in the preceding step preferably is between 3 and 8, particularly preferably between 3.5 and 7, or between 4 and 6.5, or between 4.1 and 6, in particular between 4.2 and 5.5.

Preferably, the cells are treated with gas in the culture medium of the preceding step and/or in the secretion step, in particular with air or oxygen. The gas used for the treatment preferably contains carbon dioxide. The proportion of carbon dioxide in the gas preferably is between 0 and 10% by volume, particularly preferably between 1 and 9% by volume or between 1.5 and 8% by volume, particularly preferably between 1.7 and 5% by volume. Carbon dioxide serves as a carbon source for plants and should be provided in photoautotrophic conditions.

The temperature in the preceding step and/or in the secretion step is preferably between 10° C. and 30° C., particularly preferably between 15° C. and 26° C.

The light irradiation, as measured in photon flux density (in µE), is preferably between 1 and 3.000, in particular between 100 and 2.200.

Said preceding step may be carried out over a period of 2 to 30 days. Within this period of time, an optimized production of the recombinant protein will take place.

Said step of (increasing the) secretion may be carried out over a period of at least 2 days, preferably for 3 to 120 days. Within this period of time, an optimized secretion of the recombinant proteins, as produced previously or in this step, will take place.

The two-step method is based on the semi-continuous cultivation of the plant cell culture and consists of the inoculation of the plant cells into a culture medium, the incubation with specific physical parameters and the addition of a number of medium components during the process. In the course of the process, the proteins are secreted at a defined point in time from the apoplastic space into the culture supernatant by altering the medium conditions.

The method according to the present invention is usually—but not necessarily—initiated with the inoculation of the cells (e.g. 0.1 g/l of dry biomass) into suitable bioreactor systems (wave reactor, chemostat, tube reactor, shaking flask etc.) containing the medium as well as the production of biomass up to a defined cell density (e.g. 1 to 3 g/l). By means of increasing the osmolarity, e.g. by the addition of the metal ion and the polymer (wherein in most cases the polymer alone does not cause an increase but often even a decrease in osmolarity), the secretion is initiated. In both these stages, the cells will produce and express protein. The method according to the present invention is arbitrarily scalable and may be employed in various reactors and amounts. Possible are very small bioreactors (microtiter plates), shaking flasks, 5 L chemostats, 100 L tube reactors and wave bioreactors (10 L to 500 L).

The present invention further relates to a culture medium as described above, e.g. comprising the surface-active polymer in an amount of at least 0.05% by weight and monovalent metal ions in a concentration of at least 20 mM and having an osmolarity of at least 0.32 osmol/L. The culture medium is suitable for the above-described method and may be employed therein, in particular in the step of (increasing the) secretion.

The culture medium preferably comprises nitrate ions, preferably in a concentration of at least 0.2 mM, phosphate ions, preferably in a concentration of at least 0.05 mM, sulfate ions, preferably in a concentration of at least 0.02 mM, calcium ions, preferably in a concentration of at least 0.1 mM, potassium ions, preferably in a concentration of at least 0.1 mM, or combinations thereof. The medium preferably comprises sodium ions, preferably in a concentration of at least 40 mM, or at least 60 mM, or at least 80 mM.

The present invention also relates to a dry nutritional medium mixture for reconstituting the culture medium as described in the above. By the addition of water, the nutritional medium mixture can yield the above-mentioned amounts and concentrations of said culture medium. Thus, the present invention also relates to a method for producing said culture medium by means of dissolving said ingredients in an aqueous solvent, preferably in water.

The present invention is further illustrated by the following Figures and Examples, without being limited to these specific embodiments of the present invention, however.

FIGURES

EXAMPLES

Figure 1:
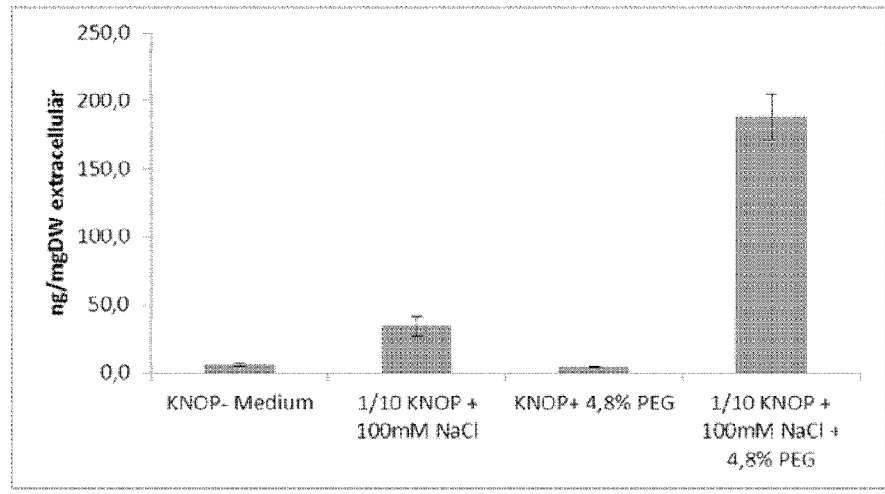
FIG. 1 shows the synergistic effects of an increase in osmolarity by the addition of NaCl and the polymer PEG on the secretion of a recombinantly produced antibody.

The present invention provides a method that enables the continuous secretion of recombinant proteins from plant cultures into the culture medium. In said method, the producing plants are submerged in a liquid culture and are photoautotrophically cultivated in specific mineral media. The culture media are optimized with respect to an optimal nutritional maintenance of moss plants, but do not per se cause the secretion of recombinantly produced larger proteins into the medium, which proteins first accumulate in the apoplast and can be measured as "intracellular" following the disruption of the moss tissue.

The apoplastic restraint of the proteins can be reversed by the addition of osmotically active substances ("secretion components"), such as NaCl and polyethylene glycol (PEG) 4000, to the culture medium. This leads to a quick release of the accumulated proteins into the medium and in the further course of the culture to a continuous and temporally immediate secretion of newly synthesized proteins.

Experimental Example: Comparison of the Protein Secretion in Erlenmeyer Cultures 500 ml Erlenmeyer flasks were filled with 180 ml of sterile Knop or WM01 medium, adjusted to pH 4.5 to 6 (2-(N-morpholino) ethanesulfonic acid buffer, "MES") and inoculated with a freshly turraxed suspension culture of Physcomitrella protonema from a recombinant strain produced by a test protein. The inoculation density was 0.1 g dry weight/l. The cultures were sealed in a sterile and gas-permeable manner and cultivated in an atmosphere supplemented with 2% $CO_2$. Upon growth to a cell density of 1 to 3 g/l, the secretion components were added in the form of a sterile concentrate. During the cultivation procedure, the parameters of culture density (g dry weight/l), intracellular and extracellular IgG titer (mg/l) were determined at regular intervals.

Results:
The following test proteins were produced:

TABLE 1

Secreted test proteins

| Protein | Molecular weight [kDa] | Secretion w/o secretion medium | Secretion with secretion medium (NaCl, PEG) |
|---|---|---|---|
| IgG | 145 | no | yes |
| Alpha-Galactosidase | 80 | no | yes |
| $VEGF_{121}$ | 50 | yes | yes |
| Epo | 30 | yes | yes |
| HSA | 67 | yes | yes |

TABLE 2

Media (all concentrations are given in mg/l. * except for MES):

| | 1 | 2 | 3 | 4 | 5 | 6 |
|---|---|---|---|---|---|---|
| Nutrit. media | KNOP | 1/10 KNOP | BM | WM01 | Murashige & Skoog | Linsmaier & Skoog |
| $KH_2PO_4$ | 250 | 25 | 250 | 500 | 170 | 170 |
| $NH_4NO_3$ | | | | | 1650 | 1650 |
| $KNO_3$ | | | | | 1900 | 1900 |
| KCl | 250 | 25 | 250 | 500 | | |
| $MgSO_4 \cdot 7H_2O$ | 250 | 25 | 250 | 500 | 180.7 | |
| $Ca(NO_3)_2 \times 4H_2O$ | 1000 | 100 | 1000 | 2000 | | |
| CaCl | | | | | 332.2 | 332.2 |
| NaCl | | | | | | |
| MES * | | | | | 5 mM | 5 mM |

In addition, microelements such as $H_3BO_3$, $FeSO_4$, Fe-NaEDTA, $CoCl_2$, $CuSO_4$, KI, $MnCl_2$, $MnSO_4$, $Na_2MoO_4$, $NiCl_2$, $Na_2SeO_3$, Zn acetate, or vitamins such as folic acid, myo-inositol, nicotinic acid, thiamine HCl, pyridoxine HCl, biotin or also glycine may be added. For fungal cultures, an additional catabolic carbohydrate source such as glucose, mannose or mannitol is added.

Example 1: Increase in Production by Means of PEG and an Increased Osmolarity An IgG antibody was expressed as described in *P. patens* using the following parameters: light rhythm [h] 16/8, initial medium KNOP, temperature 22° C., culture container: flask; medium "1/10 KNOP NaCl" containing 100 mM of NaCl in addition to medium "1/10 KNOP". Medium "KNOP PEG" and "1/10 KNOP NaCl PEG", respectively, containing 4.8% by weight of PEG-4000 in addition to medium "KNOP" and "1/10 KNOP NaCl", respectively. The results of the antibody production after 6 weeks are represented in Table 3 and in FIG. 1.

TABLE 3

PEG and NaCl (100 mM for increase in osmolarity)

| Flask | intracellular ng IgG/mg dry weight | extracellular ng IgG/mg dry weight | extra/total % |
|---|---|---|---|
| Knop, Experiment 1 | 62.3 | 4.8 | 7% |
| Knop, Experiment 2 | 88.5 | 6.6 | 7% |
| Knop, Experiment 3 | 84.1 | 6.4 | 7% |
| Average | 78.3 | 5.9 | 7% |
| 1/10 Knop NaCl, Experiment 1 | 27.3 | 29.7 | 52% |
| 1/10 Knop NaCl, Experiment 2 | 24.0 | 30.8 | 56% |
| 1/10 Knop NaCl, Experiment 3 | 19.5 | 43.1 | 69% |
| Average | 23.6 | 34.5 | 59% |
| Knop PEG, Experiment 1 | 35.9 | 4.3 | 11% |
| Knop PEG, Experiment 2 | 25.0 | 4.5 | 15% |
| Knop PEG, Experiment 3 | 33.1 | 4.5 | 12% |
| Average | 31.4 | 4.4 | 13% |
| 1/10 Knop NaCl, PEG, Experiment 1 | 27.7 | 180.7 | 87% |
| 1/10 Knop NaCl, PEG, Experiment 2 | 30.1 | 175.3 | 85% |
| 1/10 Knop NaCl, PEG, Experiment 3 | 36.2 | 208.2 | 85% |
| Average | 31.3 | 188.1 | 86% |

With the combination of NaCl and PEG an increase in productivity and secretion was observed that by far exceeded the respective effects of NaCl alone and PEG alone. A synergistic effect is thus clearly obvious.

Figure 2:
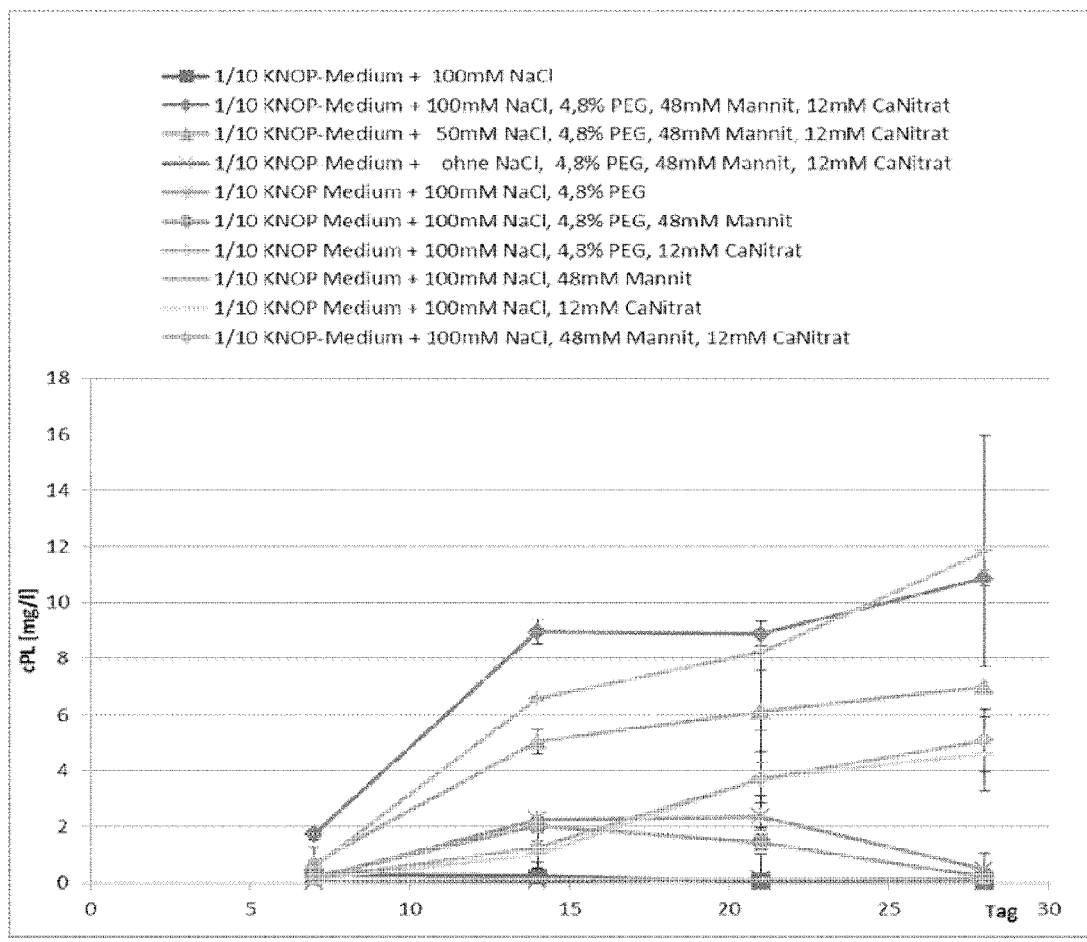
FIG. 2 shows additional production-increasing effects of mineral substances for stimulating plant growth (Ca nitrate)

Example 2: Increase in Production by Means of PEG and an Increased Osmolarity and Nitrate A lambda chain of an IgG1 antibody was expressed as described in *P. patens* using the following parameters: light rhythm [h] 16/8, initial medium KNOP, temperature 25° C., light intensity 40 µE/m²s, culture container: flask; The results of the antibody production after different time intervals are represented in Table 4 and in FIG. 2.

TABLE 4

PEG, NaCl (osmolarity) and nitrate (concentration IgG1 in µg/ml)

| Day of cultivation | 7 | 14 | 21 | 28 |
|---|---|---|---|---|
| 1/10 KNOP 100 mM NaCl medium + | 0.279 | 0.239 | 0.053 | 0.059 |
| 1/10 KNOP medium + 100 mM NaCl, 4.8% PEG, 48 mM mannitol, 12 mM calcium nitrate | 1.719 | 8.947 | 8.882 | 10.872 |
| 1/10 KNOP medium + 50 mM NaCl, 4.8% PEG, 48 mM mannitol, 12 mM calcium nitrate | 0.717 | 5.04 | 6.125 | 7.001 |
| 1/10 KNOP Medium + without NaCl, 4.8% PEG, 48 mM mannitol, 12 mM calcium nitrate | 0.048 | 0.086 | 0.123 | 0.122 |
| 1/10 + 100 mM NaCl KNOP medium, 4.8% PEG | 0.19 | 2.248 | 2.363 | 0.494 |
| 1/10 + 100 mM NaCl KNOP medium, 4.8% PEG, mannitol 48 mM | 0.214 | 2.041 | 1.453 | 0.213 |
| 1/10 + 100 mM NaCl KNOP medium, 4.8% PEG, 12 mM calcium nitrate | 0.578 | 6.574 | 8.226 | 11.83 |
| 1/10 + 100 mM NaCl KNOP medium, 48 mM mannitol | 0.043 | 0.132 | 0.12 | 0.088 |
| 1/10 + 100 mM NaCl KNOP medium, 12 mM calcium nitrate | 0.159 | 1.027 | 3.715 | 4.606 |
| 1/10 KNOP medium + 100 mM NaCl, 48 mM mannitol, 12 mM calcium nitrate | 0.185 | 1.259 | 3.704 | 5.087 |

According to these results, mannitol has no influence on the secretion behavior. Nitrate is advantageous due to the improved plant growth. In further experiments, potassium, phosphate, sulfate, or calcium ions, within a range of 1 to 10 mM, also showed positive effects that are based on an improved plant growth. In these low concentrations and without a significant increase in osmolarity no effect on the secretion could be observed.

Example 3: Different Polymers and Polymer Concentrations

Figure 3:
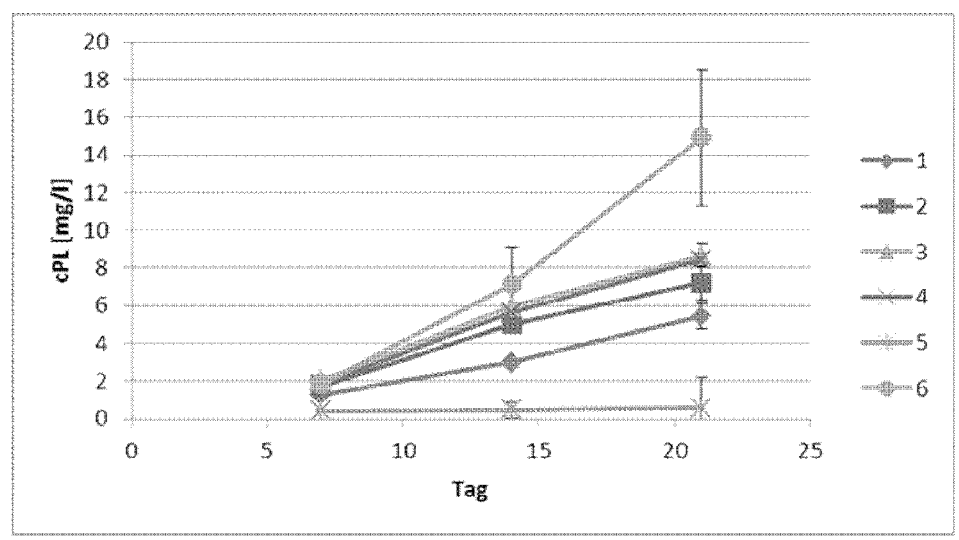
FIG. 3 shows the effects of different polymer concentrations.

A lambda chain of an IgG1 antibody was expressed as described in *P. patens* using the following parameters: light rhythm [h] 16/8, initial medium KNOP/BM, temperature 25° C., light intensity 40 µE/m²s, culture container: flask; the results of the antibody production after different time intervals are represented in Tables 5 and 6 and in FIG. 3.

TABLE 5

Medium composition and IgG production (concentrations in mM)

| Medium | 1 | 2 | 3 | 4 | 5 | 6 |
|---|---|---|---|---|---|---|
| Magnesium ions | 0.1014 | 0.501 | 0.501 | 0.501 | 0.501 | 0.501 |
| Calcium ions | 12.4235 | 14.09 | 14.09 | 14.09 | 14.09 | 14.09 |
| Chloride ion | 100 | 100 | 100 | 100 | 100 | 100 |
| Sulfate ions | 0.1059 | 0.501 | 0.501 | 0.501 | 0.501 | 0.501 |
| Nitrate ions | 24.847 | 28.185 | 28.185 | 28.185 | 28.185 | 28.185 |
| Potassium ions | 0.1837 | 0.9075 | 0.9075 | 0.9075 | 0.9075 | 0.9075 |
| Sodium ions | 100 | 100 | 100 | 100 | 100 | 100 |
| Phosphate ions | 0.1837 | 0.9075 | 0.9075 | 0.9075 | 0.9075 | 0.9075 |
| MES | 0 | 2.4705 | 2.4705 | 2.4705 | 2.4705 | 2.4705 |
| Mannitol | 48 | 48 | 48 | 48 | 48 | 48 |
| PEG [%] w/V | 4.8 | 4.8 | 1 | 0.5 | | |
| pH | 5.8 | 5.9 | 5.9 | 5.9 | 5.9 | 5.9 |
| Tween 20 [w/v] | | | | | 0.05 | 0.01 |

TABLE 6

| Results of the IgG production in μg/ml | | | |
|---|---|---|---|
| Medium No. | 7 d | 14 d | 21 d |
| 1 | 1.26 | 2.98 | 5.43 |
| 2 | 1.75 | 5.01 | 7.2 |
| 3 | 2.05 | 5.95 | 8.66 |
| 4 | 1.85 | 5.61 | 8.42 |
| 5 | 0.41 | 0.46 | 0.57 |
| 6 | 1.88 | 7.13 | 14.9 |

Based on these results it can be concluded that low concentrations of PEG do not have a negative influence on the secretion in the presence of PEG. The effect of Tween is stronger in lower concentrations (medium 6) than in high concentrations (medium 5).

The invention claimed is:

1. A method for producing a recombinant protein in plant cells, said method comprising the steps of:
   (a) growing cells having a cell wall in a first culture medium having an osmolarity of less than 0.1 osmol/L wherein the medium does not comprise a non-ionic surface-active polymer or comprises the non-ionic surface-active polymer in a maximum concentration, whereby protein accumulates in the interior of the cell or in the apoplastic space of the cell, and
   (b) then growing the cells in a second culture medium containing a combination of a nonionic surface-active polymer in a minimum concentration and monovalent metal ions and having an osmolarity of at least 0.32 osmol/L, wherein the recombinant protein is expressed in the cells and whereby the recombinant protein is secreted through the cell wall into the medium,
   wherein step (a) is carried out for a at least 2 days, and wherein for said polymer either
   (i) the maximum concentration of step (a) is 0.08% by weight and the minimum concentration of step (b) is 0.5% by weight, or
   (ii) the maximum concentration of step (a) is 0.01% by weight and the minimum concentration of step (b) is 0.1% by weight.

2. The method according to claim 1, characterized in that the secretion into the medium is effected from the apoplastic space of the cell.

3. The method according to claim 1 or 2, wherein the plant cell is a cell in a plant or in a plant tissue or a moss cell.

4. The method according to claim 1, characterized in that the cell is cultivated in a suspension culture.

5. The method according to claim 1, characterized in that the metal ion is an alkali metal ion and/or that the metal ion is present in a concentration of at least 20 mM in the medium.

6. The method according to claim 1, characterized in that the non-ionic surface-active polymer is a polyalkyl glycol.

7. The method according to claim 1, characterized in that the medium of step (b) comprises nitrate ions, phosphate ions, sulfate ions, calcium ions, potassium ions, sodium ions, or combinations thereof.

8. The method according to claim 1, characterized in that the culture medium in step (a) comprises nitrate ions, phosphate ions, sulfate ions, calcium ions, potassium ions, or combinations thereof; and/or comprises sodium ions in a maximum concentration 20 mM.

9. The method according to claim 1, characterized in that said step (a) is carried out over a period of 2 to 30 days.

10. The method according to claim 1, characterized in that said step (b) is carried out over a period of at least 2 days.

11. The method of claim 5, wherein the alkali metal is sodium.

12. The method of claim 6 wherein the polyalkyl glycol is a polyethylene glycol.

13. The method of claim 7, wherein the nitrate ions are in a concentration of at least 0.2 mM.

14. The method of claim 7, wherein the phosphate ions are in a concentration of at least 0.05 mM.

15. The method of claim 7, wherein the sulfate ions are in a concentration of at least 0.02 mM.

16. The method of claim 7, wherein the calcium ions are in a concentration of at least 0.1 mM.

17. The method of claim 7, wherein the potassium ions are in a concentration of at least 0.1 mM.

18. The method of claim 7, wherein the sodium ions are in a concentration of at least 20 mM.

19. The method of claim 1, wherein said step (a) is without said secretion.

20. The method of claim 8, wherein the medium of step (a) comprises nitrate ions in a concentration of at least 0.2 mM, phosphate ions in a concentration of at least 0.05 mM, sulfate ions in a concentration of at least 0.02 mM, calcium ions in a concentration of at least 0.1 mM, potassium ions in a concentration of at least 0.1 mM.

21. The method according to claim 1, characterized in that said step (b) is carried out over a period of 3 to 120 days.

* * * * *